(12) United States Patent
Limoli et al.

(10) Patent No.: US 11,031,111 B1
(45) Date of Patent: Jun. 8, 2021

(54) SYSTEMS AND METHODS FOR OPTIMIZING CLINICAL WORKFLOW USING A PRIORITIZATION ENGINE

(71) Applicant: WELLSHEET, INC., New York, NY (US)

(72) Inventors: Craig Limoli, Warren, NJ (US); D. Justin Larkin, Stanford, CA (US); Ryan Lee, Santa Clarita, CA (US)

(73) Assignee: WELLSHEET, INC., New York, NY (US)

( * ) Notice: Subject to any disclaimer, the term of this patent is extended or adjusted under 35 U.S.C. 154(b) by 214 days.

(21) Appl. No.: 16/106,612

(22) Filed: Aug. 21, 2018

Related U.S. Application Data

(60) Provisional application No. 62/548,208, filed on Aug. 21, 2017.

(51) Int. Cl.
| | |
|---|---|
| *G16H 10/60* | (2018.01) |
| *G06F 3/16* | (2006.01) |
| *G06N 20/00* | (2019.01) |
| *G06N 5/04* | (2006.01) |

(52) U.S. Cl.
CPC .............. *G16H 10/60* (2018.01); *G06F 3/165* (2013.01); *G06N 5/04* (2013.01); *G06N 20/00* (2019.01)

(58) Field of Classification Search
CPC .......... G16H 10/60; G06N 20/00; G06N 5/04; G06F 3/165
See application file for complete search history.

(56) References Cited

U.S. PATENT DOCUMENTS

| | | | | |
|---|---|---|---|---|
| 2014/0096037 A1* | 4/2014 | Grosz | ............... | H04N 1/00196 |
| | | | | 715/753 |
| 2015/0227710 A1* | 8/2015 | Pappada | ............... | G06Q 50/22 |
| | | | | 705/2 |
| 2016/0019352 A1* | 1/2016 | Cohen | ................... | G16H 10/60 |
| | | | | 705/3 |

OTHER PUBLICATIONS

Ed Corbett, The Real-World Benefits of Machine Learning in Healthcare, Health Catalyst (Apr. 25, 2017) (Year: 2017).*
The 5Q—Seeing is Believing: Looking at the Next Wave of Healthcare Data Visualization with Stephen Marshall, The Tincture Collective (Aug. 11, 2016) (Year: 2016).*
Julien Dumazert, Understanding the layout of webpages using automatic zone recognition, Contentsquare Engineering: Stories from the people building Contentsquare (Mar. 6, 2017) (Year: 2017).*
William Hsu et al., Context-Based Electronic Health Record: Toward Patient Specific Healthcare, 16(2) IEEE Transactions on Information Technology in Biomedicine 228-234 (Mar. 2012) (Year: 2012).*
Mi Hwa Song et al., Comparison of Machine Learning Algorithms for Classification of the Sentences in Three Clinical Practice Guidelines, 19(1) Healthcare Informatics Research 16-24 (Year: 2013).*

* cited by examiner

*Primary Examiner* — Fonya M Long
*Assistant Examiner* — Jordan L Jackson
(74) *Attorney, Agent, or Firm* — Baker Botts L.L.P.

(57) ABSTRACT

The disclosed subject matter is directed to systems and methods for processing multiple sources of data into a clinical data prioritization and visualization framework that enhances and expedites clinical workflow.

22 Claims, 5 Drawing Sheets

FIG. 5

SYSTEMS AND METHODS FOR OPTIMIZING CLINICAL WORKFLOW USING A PRIORITIZATION ENGINE

CROSS REFERENCE TO RELATED APPLICATION

This application claims priority to U.S. Provisional Patent Application No. 62/548,208, entitled "Systems and Methods for Optimizing Clinical Workflow Using a Prioritization Engine" which was filed on Aug. 21, 2017, the entire contents of which are incorporated by reference herein

BACKGROUND

Electronic Health Records (EHR) are the current means by which physicians view patient information. However, EHR displays provide patient information in a static display and cannot be adjusted and/or customized such that patient information can be displayed in a customized manner for different clinician users, patients, or to be suited to an appropriate relevant clinical context. With an ever-increasing volume of patient data, clinicians sifting through current EHR systems are being bombarded with inefficient and static displays of patient data from which it is time consuming to extract the relevant patient information. Clinicians wading through such current EHR systems under time constraints are often frustrated with the EHR experience, are prone to miss key patient details, and make treatment decisions that often fail to optimize care quality.

Accordingly, there is an increasing need to provide clinicians with an efficient display of patient information configured to efficiently process patient information to emphasize the most relevant aspects of such patient data for timely and effective point-of-care decisions.

SUMMARY

The disclosed subject matter is directed to systems and methods for processing multiple sources of data into a clinical data prioritization and visualization framework that enhances and expedites clinical workflow.

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, a computer-implemented self-enhancing clinical data prioritization and visualization system is disclosed. The system can include a combiner module configured to retrieve information relating to a clinical context of a patient visit from a plurality of information sources. The system can include a prioritization module configured to prioritize contents of a display for a context-driven interface. The prioritization module can be configured to perform experience-driven statistical inference to generate priority estimates for different clinical information. The priority estimates can be used to determine placement of a plurality of visual blocks representing clinical data points within the context-driven interface. The prioritization module can also be configured to perform machine interpretation of clinical guidelines to adjust the priority estimates for different clinical information by applying a plurality of document-driven rules to adjust the priority estimates generated by the experience-driven statistical inference. The system can also include a display module configured to generate the context-driven interface comprising a plurality of visual blocks arranged in a prioritized order based on their adjusted priority estimates for display.

For purpose of illustration and not limitation, the combiner module can be further configured to retrieve analytics information from analytics data sources to assemble an analytics model. The combiner module can retrieve patient data from patient data sources and can also combine the analytics model with the patient data for display in the context-driven interface.

For purpose of illustration and not limitation, the prioritization module can be further configured to receive user inputs from the context-driven interface. The prioritization module can monitor outcome metrics of the treatment generated by the system through usage of the context-driven interface. The prioritization module can also adjust the priority estimate of the plurality of visual blocks based on the user inputs with the context-driven interface and the outcome metrics. In some embodiments, the user inputs can comprise voice inputs to the context-driven interface. The priority estimate of the plurality of visual blocks can be adjusted based on whether the user input is a voice input.

For purpose of illustration and not limitation, the prioritization module in performing the experience-driven statistical inference can be further configured to prioritize the retrieved information relating to a clinical context of a patient visit to a clinical context by fitting a non-parametric machine learning model to estimate the priority of observed data points in the retrieved information and unobserved data points in the retrieved information from clinical context information based on patterns from historical physician behaviors and contextually important patient outcomes.

For purpose of illustration and not limitation, the prioritization module in performing the experience-driven statistical inference can be further configured to encode features of the retrieved information relating to a clinical context of a patient visit related to the clinical context into binary features to be input into a machine learning model. The prioritization module can also instruct the machine learning model to generate priority estimates of observed data points using the encoded features to estimate priority of observed clinical data points. The prioritization module can also iteratively adjust the machine learning model using a loss calculated by comparing the priority estimates against a priority index comprising historical physician behaviors and patient outcomes. In response to determining that iterative adjustment of the machine learning model is complete, the prioritization module can determine priority estimates for observed and unobserved data points in real time to be used to perform the machine interpretation of clinical guidelines.

For purpose of illustration and not limitation, the prioritization module in performing the machine interpretation of clinical guidelines can be further configured to adjust the priority estimates of each of the plurality of visual blocks in the context-driven interface from an experience-driven statistical inference based on dimensions of relevancy, abnormality, and quality. The relevancy dimension can indicate an extent to which a given data point is associated with a specified clinical context. The abnormality dimension can indicate whether the quantity associated with a clinical data point is unusual in magnitude for the specified clinical context. The quality dimension can indicate an extent to which a clinical data point is expected to improve quality of care in the specified clinical context.

For purpose of illustration and not limitation, the prioritization module in performing the machine interpretation of clinical guidelines can be further configured to apply documented clinical guidelines retrieved by the combiner module to an observed clinical context to identify suggested care components along the dimensions of relevancy, abnormality, and quality. In some embodiments, the prioritization module can be further configured to extract, from the documented clinical guidelines, features based on the dimension of relevancy by tagging specific text in the documented clinical guidelines as recommendations and other text in the documented clinical guidelines as context and extracting features based on at least one or more of the presence of n-gram word combinations and by using natural language processing algorithms. In some embodiments, the prioritization module can be further configured to extract, from the documented clinical guidelines, features based on the dimension of abnormality by identifying specific diagnostics, medications, and prescriptions in the text of the documented clinical guidelines and parsing their associated normal values and mapping the identified specific diagnostics, medications, and prescriptions from the text to an appropriate treatment to adjust the priority estimates generated by the experience-driven statistical inference. In some embodiments, the prioritization module can be further configured to extract, from the documented clinical guidelines, features based on the dimension of quality codifying conditions when specific diagnostics, medications, and prescriptions in the text of the documented clinical guidelines are applicable by evaluating a quantitative value associated with each of the specific diagnostics, medications, and prescriptions in the context of a visiting patient and increasing the priority estimate for the relevant codified condition when patient information corresponding to the visiting patient matches the codified condition.

For purpose of illustration and not limitation, the combiner module can be further configured to retrieve patient information by parsing audio data describing the patient. The audio data can be retrieved from one or more of audio recordings received from patients, physician audio recordings, and/or monitored audio dialog between doctors and patients.

In accordance with another aspect of the disclosed subject matter, a computer-implemented method for performing self-enhancing clinical data prioritization and visualization is disclosed. The computer-implemented method can include retrieving information relating to a clinical context of a patient visit from a plurality of information sources. The computer-implemented method can include prioritizing, by a processor, contents of a display for a context-driven interface by performing experience-driven statistical inference to generate priority estimates for different clinical information and by performing machine interpretation of clinical guidelines to adjust the priority estimates for different clinical information by applying a plurality of document-driven rules to adjust the priority estimates generated by the experience-driven statistical inference. The priority estimates can be used to determine placement of a plurality of visual blocks representing clinical data points within the context-driven interface. The computer-implemented method can include generating, by the processor, a display of the context-driven interface comprising a plurality of visual blocks arranged in a prioritized order based on their adjusted priority estimates.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 5 depicts an exemplary display of an enhanced patient information display providing a dynamically generated display of patient information that has been generated by the disclosed systems and methods to be customized for a specific patient and a specific context in accordance with one or more embodiments of the disclosed subject matter.

DETAILED DESCRIPTION

Systems and methods for using computer-implemented self-enhancing clinical data prioritization and visualization are disclosed herein. In particular, the disclosed subject matter is directed to systems and computer-implemented data analytics methods of translating multiple sources of data into a clinical data prioritization and visualization framework that enhances and expedites clinical workflow. According to some embodiments, based on a set of inputs (e.g., physician specialty, past behavior of user, past behavior of similar users, clinical guidelines, patient profile, previous outcomes, monitored dialogs between clinician and patient, voice input from a clinician, etc.), the disclosed systems and methods can be configured to assign values across multiple dimensions, including urgency and relevancy, to the patient framework which can then be applied to the patients' clinical data. According to some embodiments, these assigned values can be used to create a rigorous methodology for surfacing the most important and/or relevant pieces of information to physicians, thereby enabling increased and/or improved expeditious data review and better treatment decision making than currently available EHR systems.

Exemplary embodiments directed to the disclosed subject matter are described below, with reference to FIGS. 1-5, for purposes of illustration, and not limitation.

Figure 1:
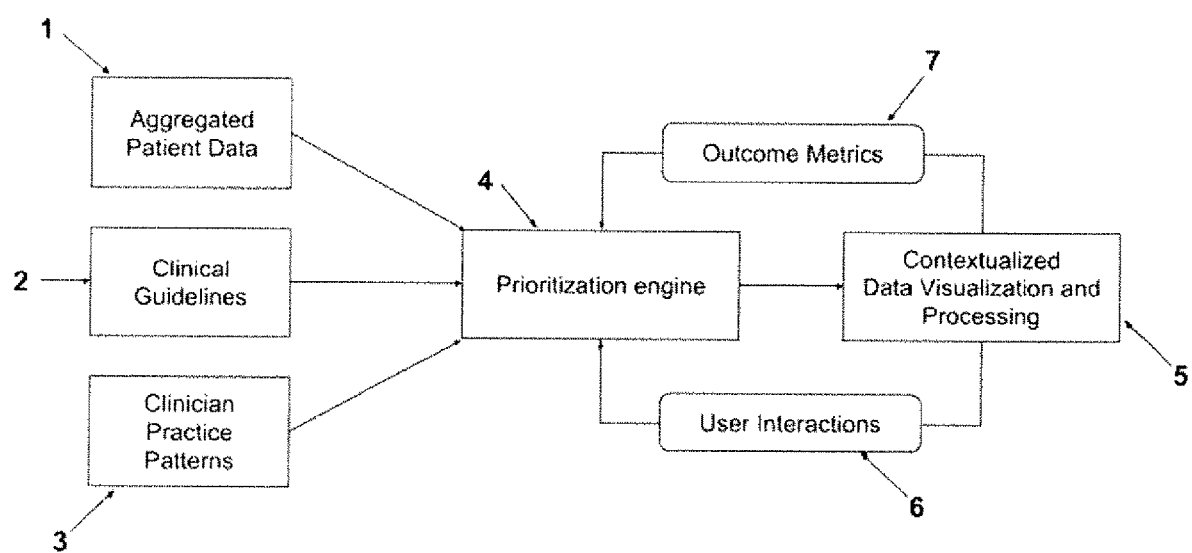
FIG. 1 depicts an exemplary diagram of a system for prioritizing clinical information for each individual physician-provider interaction in accordance with one or more embodiments of the disclosed subject matter.

FIG. 1 depicts an exemplary diagram of a system for prioritizing clinical information of each individual physician-provider interaction. In some embodiments, clinical information to be used by the system can be retrieved from at least three primary sources of clinical information. The first source of clinical information is aggregated patient data 1, which is the medical history of the patient, and can be extracted from traditional Electronic Health Record systems. The second source of clinical information, which is the clinical guidelines 2, can be retrieved from several different (e.g., tens of thousands of) documented best practice guidelines for treating a comprehensive set of conditions, which are stored in various networked databases. These clinical guidelines 2 can be processed using natural language processing (NLP) methods to parse the content of the guidelines to be applied to the disclosed context-driven interface 5. In some embodiments, in addition to parsing documented best practice guidelines from documented sources, the clinical guidelines 2 can be supplemented with physician voice input guidelines. For example, a particular physician may desire to supplement clinical guidelines by dictating certain specific guidelines to a recording device and/or an input device including a microphone. The physician's voice input can be processed by processing and/or parsing the captured audio signal using various NLP methods and can be used to supplement the rest of the clinical guidelines 2. The third source of clinical information, which is aggregated historical data 3, can be acquired at least by processing through patients' billed claims. By processing patients' historical billed claims, the disclosed system can determine how patients have been historically treated for their various conditions over years.

In some embodiments, data from these sources of information can be extracted via application programming interfaces (APIs) using API-based processes for authentication and for an extract, transform, and load data warehousing process that can retrieve data from the source systems and place it into a data warehouse. In some embodiments, data can also be consolidated across multiple systems via a reconciliation process that identifies the unique data for the patient contained in the full set of systems. In some embodiments, Health Information Exchange (HIE) data can also be extracted via a standard methodology.

In some embodiments, a prioritization engine 4 can process these three data sources to produce a context-driven interface 5 that can provide value to clinicians by surfacing the key patient information needed by the clinicians to know about the visiting patient they are treating, how similar other patients have been successfully treated in the past, and which approach(es) the clinical guidelines 2 recommend in the relevant clinical context. Such relevant information can be generated for display as the context-driven interface 5 in an enhanced patient information display. By monitoring the clinicians' user interactions 6 with context-driven interface 5 and by monitoring the outcome metrics 7 of the course of the treatment generated by the system through usage of the context-driven interface 5, the system can continuously refine and improve the context-driven interface 5 by directing the user interactions 6 with context-driven interface 5 and the outcome metrics 7 back into the prioritization engine 4 through a feedback loop.

According to an exemplary embodiment, the patient-owned data can be collected through a two-factor authentication process. For example, once the patient enters a medical facility, the patient can be notified (e.g., via text, email, smartphone notification, phone call, etc.) that they can send their provider their information by opting in and replying "Yes." If the patient accepts, his or her data can be transmitted instantly from the Health-Kit or other health app to a "Patient Data Combiner" module. The "Patient Data Combiner" module can combine information from analytics data sources (e.g., practice patterns such as MIMIC and CMS data, guidelines such as Medscape and specialty based guidelines, and user analytics such as the Amazon Web Services toolset) to assemble an analytics model. The "Patient Data Combiner" module can also combine data about the patient across multiple different patient data sources such as accessible EHR systems, HIE, and patient-owned data sources. Next, the "Patient Data Combiner" module can be configured to combine the analytics model with the patient data to produce the end result for the user interface of the context-driven interface 5.

In some embodiments, the "Patient Data Combiner" module can combine patient information extracted from patient voice input data into the patient data. For example, audio monitoring devices in doctors' offices can capture the audio dialog between patients and their doctors. Such audio data can be parsed using various NLP methods to extract relevant patient data from such dialogs to supplement the patient data for each respective client. Additionally or alternatively, a physician can record audio during and/or after the patient visit, which can be similarly recorded by an audio recording device and parsed to be added to the patient data for the corresponding patient that the physician is describing. In some embodiments, the "Patient Data Combiner" can also combine, into the patient data, voice data captured from patients describing additional information (e.g., medical history, prescription information, and any other information relevant to the clinical context). For example, patients can record into an audio recording device (e.g., their own smartphones) an audio recording describing such relevant additional information. The "Patient Data Combiner" can query for such additional patient audio recordings, physician audio recordings about patients, and audio dialog between doctors and patients from various audio recording sources and/or parsed audio databases and can process such audio data into the patient data for a given patient. In some embodiments, the "Patient Data Combiner" can add metadata describing the context and/or source of the audio recording (e.g., whether the audio data originated from patient audio recordings, physician audio recordings about patients, and/or audio dialog between doctors and patients, etc.). Such metadata can be used by the prioritization engine 4 in prioritizing which type of patient data to prioritize based on the relevancy of the context and/or source of the audio recording to the clinical context.

Figure 2:
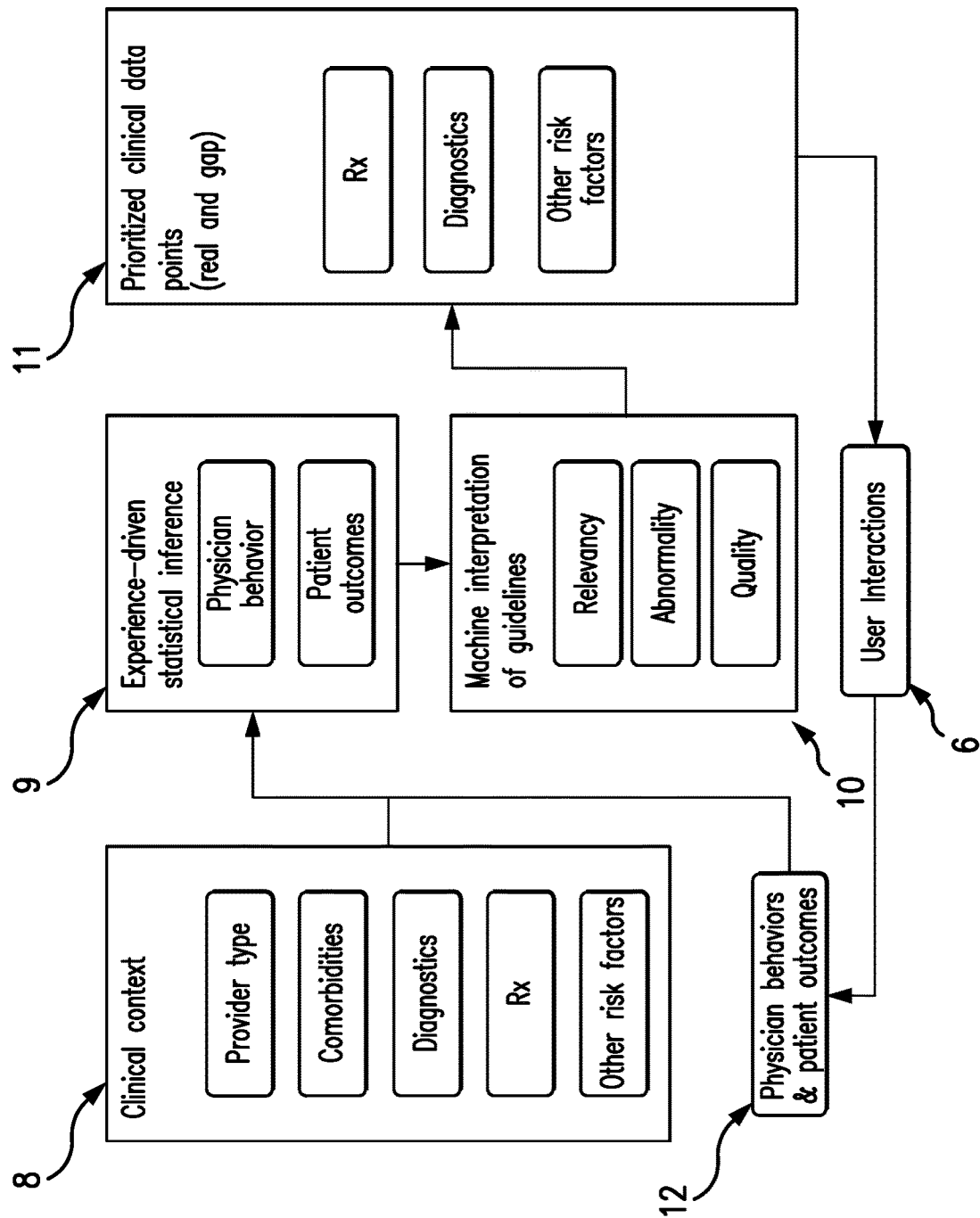
FIG. 2 depicts an exemplary diagram of a dataflow associated with the prioritization engine in accordance with one or more embodiments of the disclosed subject matter.

FIG. 2 depicts an exemplary diagram of the dataflow associated with the prioritization engine 4. In an exemplary and non-limiting embodiment, the prioritization engine 4 can be configured to accept various types of information relating to the clinical context 8 of the patient's visit. In some embodiments, these types of information relating to the clinical context 8 can include provider type, comorbidities, diagnostics, medical prescriptions (i.e., Rx), and other risk factors. In some embodiments, the prioritization engine 4 can prioritize the contents of the display for context-driven interface 5 by performing experience-driven statistical inference process 9 and machine interpretation of guidelines process 10. The prioritization estimates generated by the prioritization engine 4 can be used to determine the placement of tiles (i.e., visual blocks containing clinical resources) representing various clinical data points within the context-driven interface 5. These tiles can represent either historical data ("real tiles") or potential care gaps ("gap tiles"). The prioritization process for real tiles and gap tiles can be similar, with notable differences as described below.

In some embodiments, the prioritization engine 4, while performing an experience-driven statistical inference process 9, can prioritize the clinical context 8 by fitting a non-parametric machine learning model to estimate the priority of real (i.e., observed) and gap (i.e., not yet observed) data points from the clinical context information 8 based on patterns from historical physician behaviors and/or contextually important patient outcomes 12. The experience-driven statistical inference process 9 is described in greater detail below in connection with FIG. 3. This priority estimate can then be determined through the machine interpretation of guidelines process 10, which overlays a series of documentation-driven rules to adjust the inference-produced estimates. The prioritization engine 4 performing a machine interpretation of guidelines process 10 can output the final priority estimates 11, hereinafter also referred to as the prioritized clinical data points 11, for real (i.e., observed) and gap (i.e., not yet observed) data points, for visual consumption. The generated prioritized clinical data points 11 can include medical prescription (i.e., Rx), diagnostics, and other risk factors. The prioritization engine 4, while performing the machine interpretation of guidelines process 10 can process and/or adjust the tile-level priorities of each displayed tile in the context-driven interface 5 from an experience-driven statistical inference based on dimensions of relevancy, abnormality, and quality as described in greater detail below in connection with FIG. 4. In some embodiments, user interactions 6 with the prioritized clinical data points 11 can be monitored and/or recorded and appended to the set of historical physician behaviors and patient outcomes 12 in order to further enhance the statistical inference process 9. In some embodiments, audio commands received from the user of the context-driven interface 5 can be processed and used to supplement the other forms (e.g., typed input, clickstream data, etc.) of user interactions 6.

Figure 3:
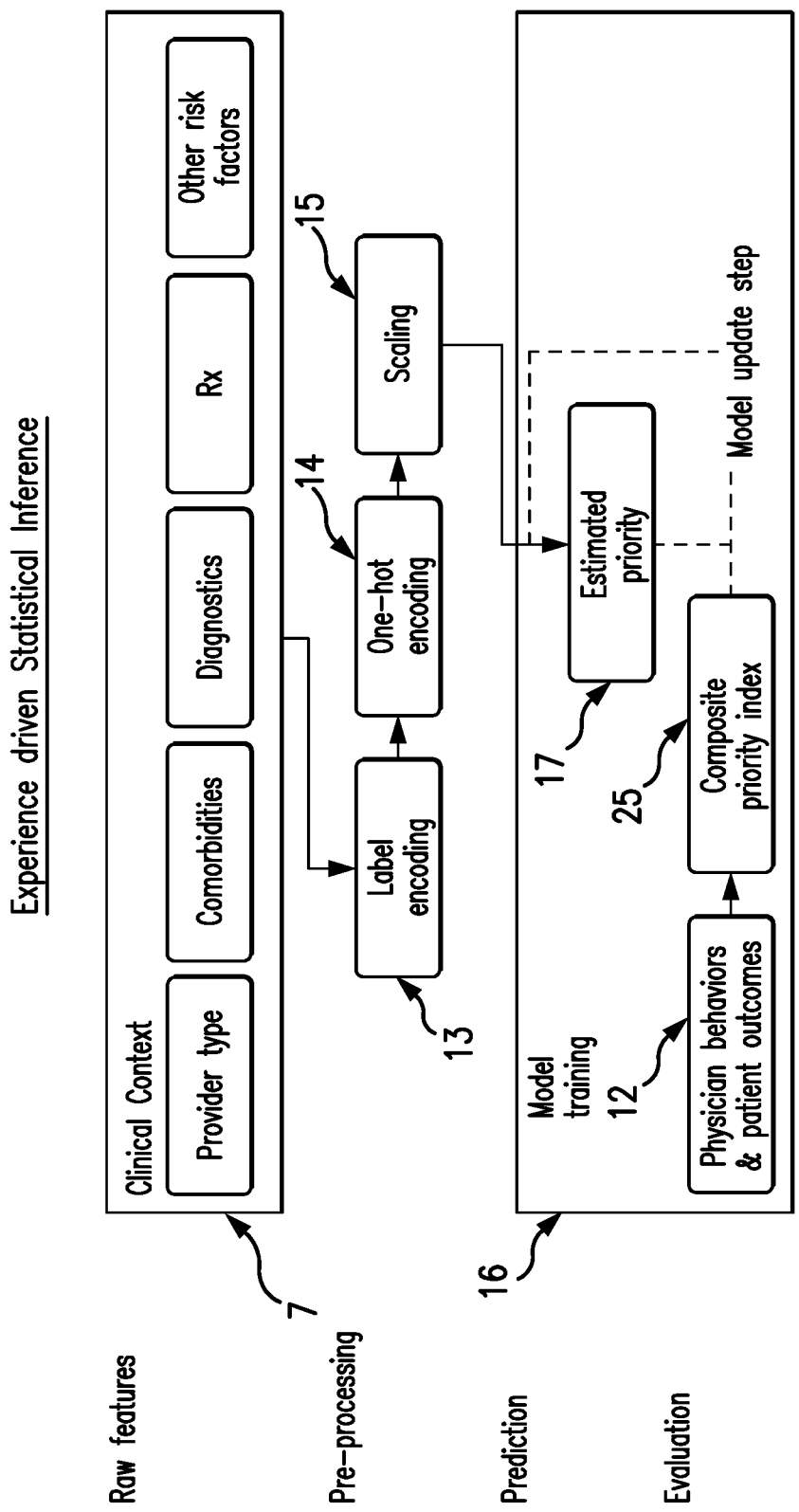
FIG. 3 depicts an exemplary process for analyzing clinical practice patterns by which the disclosed system can predict the information needed for a particular clinician in a specific context in accordance with one or more embodiments of the disclosed subject matter.

FIG. 3 depicts an exemplary embodiment of the experience-driven statistical inference process 9, which can use a non-parametric machine learning model to estimate clinical data priority through iterative model fitting. In some embodiments as illustrated by exemplary embodiment depicted by FIG. 3, the experience-driven statistical inference process 9 can include at least four stages.

In the first stage of the experience-driven statistical inference process 9, the prioritization engine 4 can gather clinical context data points 7 as raw features from various external datasets. Similarly, in some embodiments, physician behaviors and patient outcomes 12, used to construct the model target variable, can be sourced from a combination of external data sets, audio data (e.g., audio data originating from patient audio recordings, physician audio recordings about patients, and/or audio dialog between doctors and patients), and historical user data. In some embodiments, the prioritization engine 4 can create a data table where each row represents one historical visit and each column represents a historical attribute related to that visit (e.g., provider specialty, diagnoses made prior to time of visit, etc.). The prioritization engine 4 can merge in data related to actions taken during that visit as new columns. Such merged data can serve as target variables (i.e., variables that will be predicted in a live setting).

In the second stage of the experience-driven statistical inference process 9, the prioritization engine 4 can pre-process the raw features in a series of steps. For example, the categorical features can be label-encoded into discrete integers 13 and then encoded into individual binary features through one-hot encoding 14 so that they can be interpreted correctly by the machine learning model. In some embodiments, real-valued features can be scaled by a scaling process 15 to unit variance and zero mean in order to ensure proper convergence of the optimization algorithm. In an exemplary embodiment, the prioritization engine 4 performing the experience-driven statistical inference process 9, can convert columns containing categorical (e.g., text) variables into individual yes and no columns, represented as 1s and 0s. For numerical columns, of the experience-driven statistical inference process 9, the prioritization engine 4 can be configured to subtract the mean of that column and divide by the standard deviation of that column.

In the third stage of the experience-driven statistical inference process 9, the prioritization engine 4 can direct a selected model 16 (e.g., gradient boosting regressor, neural network, etc.) to input the resulting processed features to estimate the priority 17 of various real clinical data points. The estimate produced by the model 16 can be compared against a composite priority index 25, comprising historical physician behaviors and patient outcomes 12. The loss from this comparison can be used to iteratively fit the model 16 by directionally tuning the relevant model parameter in a model update step.

In some embodiments, the model 16's loss function can be determined by the requirements of the selected model (e.g., gradient boosting regressor, neural network) and the associated optimization algorithm (e.g., stochastic gradient descent, RMSprop). The selection of the model form and the specification of model hyperparameters (e.g., regularization, number of layers, and number of trees) can be set on the basis of mean absolute out-of-sample prediction error. In some embodiments, the priority index 25 can be continuous over the range [0, 1], with higher values indicating higher priority, and can be constructed by non-linearly combining historical physician behaviors and patient outcomes 12 based on medical expertise. Once this iterative fitting is completed, the model 16 can infer priority estimates 17 for real (i.e., observed) data points and gap (i.e., unobserved) data points in real time, and these estimates can be sent to the machine interpretation of guidelines process 10.

In some embodiments, a variety of machine learning techniques can be used for the selected model 16. For purposes of illustration and not limitation, the selected model 16 can be a neural network. According to an exemplary embodiment, the model 16 can first split the pre-processed features into an 80% sample used to train the model 16 and a 20% sample used to evaluate the model 16. An initial model (e.g., having 3 fully connected layers, 100 nodes each, leaky ReLU activation function) can be constructed with initial weights drawn from a random normal distribution. In the prediction stage, the 80% sample can be fed through the neural network, which produces an estimated priority 17 through a series of matrix multiplication operations using the model weights and nonlinear transformations through a selected activation function (e.g., ReLU) for each layer of the network. The estimated priority 17 can be compared to the actual priority for that visit to calculate a model error (e.g., using the mean absolute difference). The actual priority can be constructed for each visit by combining the historical conditional frequency for that observation with historical user event data. If the model error is not close to zero, the model weights can be adjusted in the direction that would decrease the priority error using stochastic gradient descent and backpropagation. The 80% sample can then be fed through the neural network again for further adjustments.

In the fourth stage of the experience-driven statistical inference process 9, the prioritization engine 4 can evaluate the model. In this model evaluation stage, if the model error is close to zero, the 20% sample can be fed through the network to estimate the out-of-sample priority. The estimates can be compared to the actual priorities of the same sample. If the resulting difference is not close to zero, the neural network can be re-specified (e.g., by increasing or decreasing the number of nodes) and the 80% sample can be fed through again. Once an appropriate model has been constructed, the resulting neural network can be run at real-time to predict priorities for patient visits by feeding the relevant attributes for each new visit forward through the network.

Figure 4:
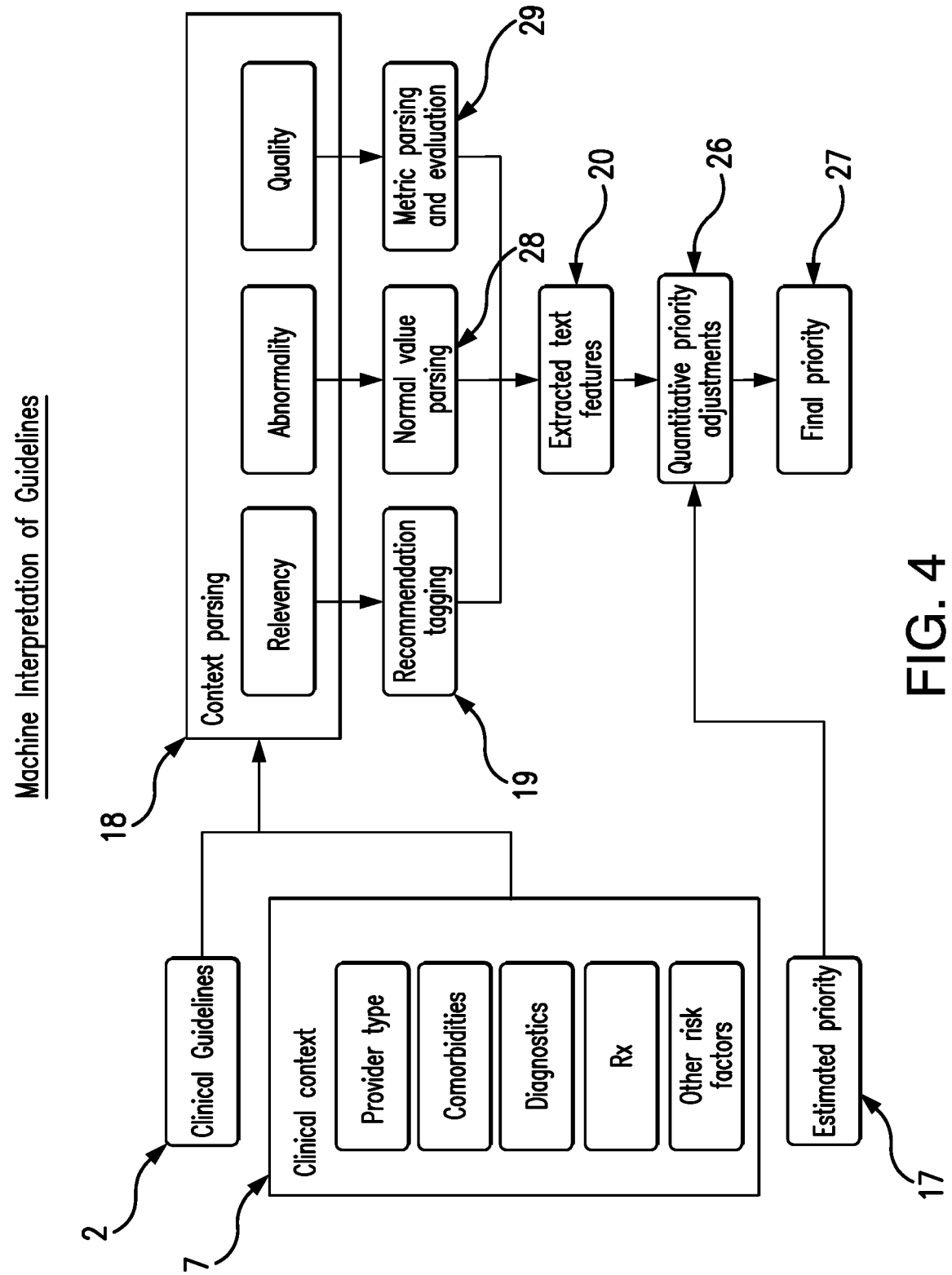
FIG. 4 depicts an exemplary process for processing clinical guidelines to predict the best course of treatment for a patient in accordance with one or more embodiments of the disclosed subject matter.

FIG. 4 depicts an exemplary process for processing clinical guidelines to predict the best course of treatment for a patient. As illustrated by the exemplary embodiment depicted by FIG. 4, the prioritization engine 4 can implement the machine interpretation of guidelines process 10 to adjust the estimated priorities 17 from the experience-driven statistical inference process 9 for specific documented guidelines. The prioritization engine 4, implementing the machine interpretation of guidelines process 10, can apply documented clinical guidelines 2 to an observed clinical context 7 to identify suggested care components along several dimensions such as relevancy, abnormality, and quality. As referred to herein, relevancy can indicate the extent to which a given data point is associated with, and specific to, the given clinical context (e.g., comorbidities, age, medications, etc.). As referred to herein, abnormality can indicate whether the quantity associated with a clinical data point is unusual in magnitude for the given context. As referred to herein, quality can indicate the extent to which a clinical data point is expected to improve the quality of care in the given context. Relevancy and quality can be defined for both real and gap data points, while abnormality can only be defined for real data points and/or real tiles as there can be no values associated with potential care gaps.

In some embodiments, each guideline can be first parsed for context and/or the set of criteria that indicate when the guideline applies 18 (e.g., patient characteristics, previous diagnoses, etc.). In connection with certain embodiments, relevancy features can then be obtained and/or derived from medical guidelines texts. In some embodiments, within the texts, relevancy features can be extracted by tagging specific text tokens as recommendations 19 and others as context and then extracting features based on the presence of n-gram word combinations and/or by using other natural language processing algorithms (e.g., word embeddings). For example, the prioritization engine 4 can create two data tables, where the rows represent one guideline and/or an individual section of a guideline. The columns of the first table, directed towards guideline context, can represent contextual features (e.g., diagnosis codes. medical specialty. etc.) which would be observable prior to the patient visit. The columns of the second table, directed towards guideline actions, can represent discrete actions (e.g., diagnostic lab codes, medication codes, etc.) that could be performed in response to the associated context. For each cell in both tables, the relevance of the column's text description to the index text can be extracted using natural language processing algorithms (e.g., TF-IDF). In an exemplary embodiment, at runtime the prioritization engine 4 can sum the columns relevant to the patient visit in the guideline context table for each row to identify the most relevant guidelines. Next, the prioritization engine 4 can sum each column in the guideline actions table across all relevant rows to determine which actions are most relevant to the context of the patient visit. Next, the prioritization engine 4 can increase the priority score in proportion to the sum.

In some embodiments, the prioritization engine 4 can extract abnormality features by identifying specific diagnostics, medications, and/or prescriptions in guidelines text and parsing their associated normal values 28. The normal values can be obtained from a set of standards indicating a range of values which are considered normal. For each standard, the lower and upper bounds can be extracted from the text and associated with a specific diagnostic or prescription. The key metric (e.g., relevant diagnostic or medication) from the text can be identified and mapped to the appropriate code (e.g., treatment, diagnostics and medications). These extracted features 20 can then be mapped to specific quantitative priority adjustments 26 relating to the inference-produced estimated priorities 17 to produce the final priority estimates 27 for visualization in the context-driven interface 5. In some embodiments, during runtime, the prioritization engine 4 can check each of the patient's diagnostics and medications against the set of codified standards and can increase the priority score if any observed values fall outside of the associated normal range.

In some embodiments, the prioritization engine 4 can obtain text descriptions of quality care metrics (e.g., MIPS). The quality features can be extracted by parsing text descriptions of metrics associated with each guideline. For each metric, the prioritization engine 4 can extract and codify conditions for when the metric is applicable can be extracted by evaluating that metric's quantitative value 29 in the context of the visiting patient (e.g., based on the required age and diagnoses). The prioritization engine 4 can identify the key metric from the text and map to the appropriate code (e.g., treatment, diagnostics, and medications). In some embodiments, during runtime, the prioritization engine 4 can check the patient visit details against the conditions for each metric. For each matching metric, the prioritization engine 4 can increase the priority scores for the relevant codes.

Figure 5:
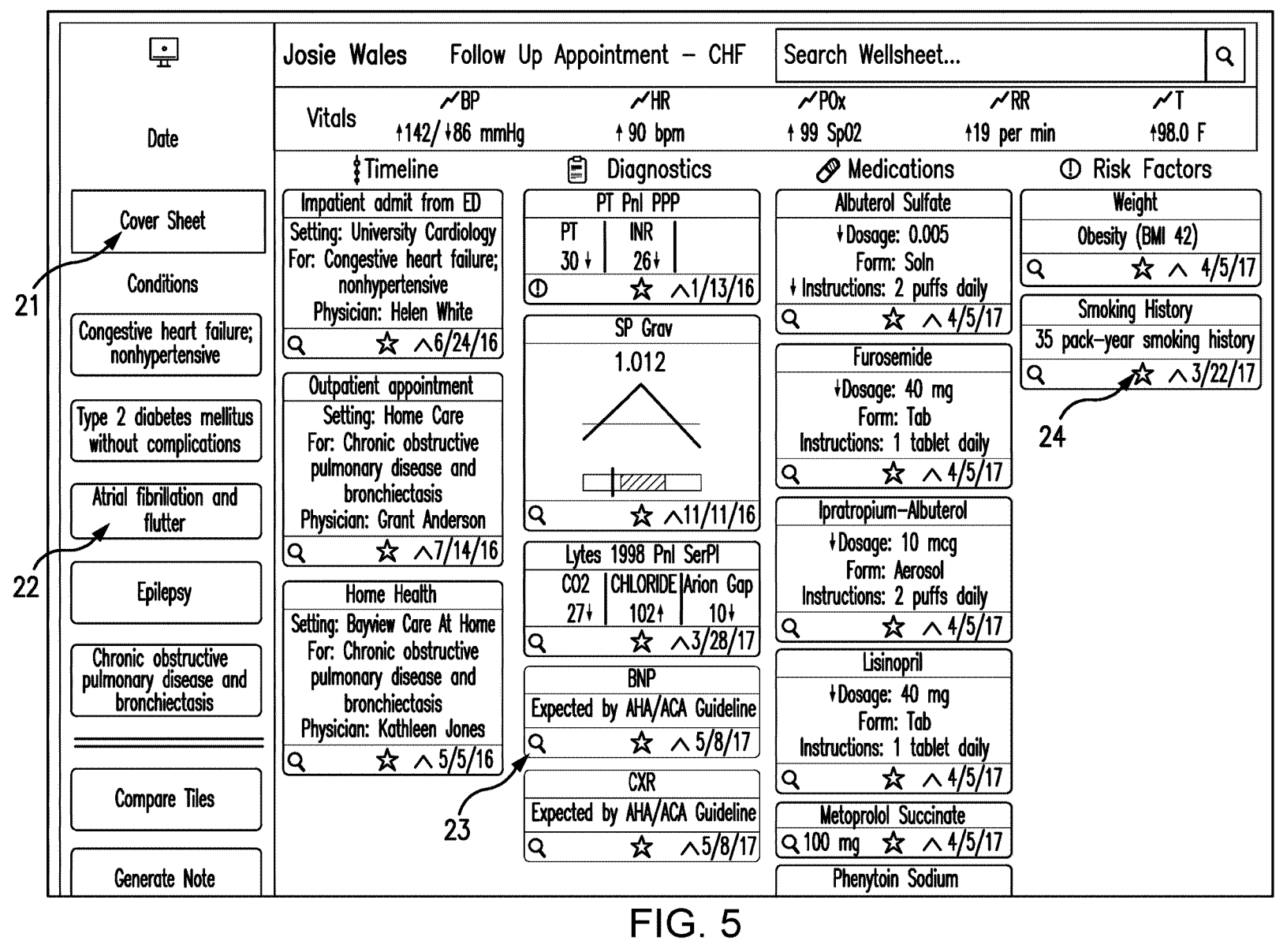

FIG. 5 depicts an exemplary embodiment of the context-driven interface 5 that serves as both the user-facing manifestation of the prioritized data and a user-action capturing mechanism to generate data about physician practice patterns. In some embodiments, the context-driven interface 5 can be configured to perform predictive tile prioritization. For example, the user interface of the context-driven interface 5 can customize the sequence of tiles (i.e., visual blocks containing clinical resources) on a patient by patient basis to surface the most critical indicators to the top of the view of the user interface. The context-driven interface 5 can be configured to generate a different prioritization of tiles for each condition the patient has been diagnosed with. The priority of a tile can be based on at least one or more the recency of the tile's information, the abnormality of diagnostic values, whether the tile's information is sourced from voice data related to a patient visit, and/or the relevance of a tile's content to a condition, which can be calculated based on the prevalence of key terms in guidelines relating to that condition.

In some embodiments, the user interface of the context-driven interface 5 can be configured to predictively collapse tiles that are less relevant to a condition and/or predictively collapse tiles that a user has previously collapsed, a process that can also be referred to as "predictive tile scaling." The modular layout of data in the user interface can allow the user (e.g., the clinician) to easily customize the view of a patient for their needs by rearranging tiles starring or un-starring 24 tiles, expanding or collapsing the tiles, and/or through a host of other user interactions with the user interface. These user interactions 6 can provide training data for the machine learning model to improve itself as users interact with the context-driven interface 5. The user interactions 6 can be in the form of typed input, click input, and/or voice input between the user of the context-driven interface 5 and the context-driven interface 5. As illustrated in FIG. 5, the CoverSheet element 21, when activated, can highlight the collection of starred tiles that should represent all of the key indicators from the aggregated patient data 1 based on the prioritization engine's 4 interpretation of the clinical guidelines 2 and clinician practice patterns 3. As illustrated in FIG. 5, the problem list 22 is a mechanism in the user interface of the context-driven interface 5 configured to focus in on a particular disease of the patient being seen by the clinician user, using each disease as a reference point for running the prioritization engine 4 to hone on the key indicators each of those diseases.

In some embodiments, the context-driven interface 5 can be configured to generate a different list of potential gaps in care for each condition a patient has been diagnosed with based on practice patterns, clinical practice guidelines, and quality requirements. A list of practice pattern-based care gap tiles can be generated by a predictive model based on key clinical features, such as comorbidities and demographics. As illustrated in FIG. 5, "gap tiles" 23 can indicate calls to action to further enable the user to generate an order for a lab or procedure to close the gap, which serves to reinforce their importance in that context.

In some embodiments, the user interface of the context-driven interface 5 can be configured to generate custom "Diagnostic Comparison" tiles, which can compare data points across pertinent diagnostics for patients and physicians. The diagnostics being compared can be selected based on a patient's set of conditions, a physician's specialty, a physician's practice patterns, and the diagnostics tiles a physician has previously chosen to compare using the "Compare Tiles" element 30.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

Although one or more embodiments have been described herein in some detail for clarity of understanding, it should be recognized that certain changes and modifications can be made without departing from the spirit of the disclosure. The embodiments described herein can employ various computer-implemented operations involving data stored in computer systems. For example, these operations can require physical manipulation of physical quantities-usually, though not necessarily, these quantities can take the form of electrical or magnetic signals, where they or representations of them are capable of being stored, transferred, combined, compared, or otherwise manipulated. Further, such manipulations are often referred to in terms, such as producing, yielding, identifying, determining, or comparing. Any operations described herein that form part of one or more embodiments of the disclosure can be useful machine operations. In addition, one or more embodiments of the disclosure also relate to a device or an apparatus for performing these operations. The apparatus can be specially constructed for specific required purposes, or it can be a general purpose computer selectively activated or configured by a computer program stored in the computer. In particular, various general purpose machines can be used with computer programs written in accordance with the teachings herein, or it can be more convenient to construct a more specialized apparatus to perform the required operations.

The embodiments described herein can be practiced with other computer system configurations including hand-held devices, microprocessor systems, microprocessor-based or programmable consumer electronics, minicomputers, mainframe computers, and the like.

One or more embodiments of the present disclosure can be implemented as one or more computer programs or as one or more computer program modules embodied in one or more computer readable media. The term computer readable medium refers to any data storage device that can store data which can thereafter be input to a computer system-computer readable media can be based on any existing or subsequently developed technology for embodying computer programs in a manner that enables them to be read by a computer. Examples of a computer readable medium include a hard drive, network attached storage (NAS), read-only memory, random-access memory (e.g., a flash memory device), a CD (Compact Discs)—CD-ROM, a CD-R, or a CD-RW, a DVD (Digital Versatile Disc), a magnetic tape, and other optical and non-optical data storage devices. The computer readable medium can also be distributed over a network coupled computer system so that the computer readable code is stored and executed in a distributed fashion.

Although one or more embodiments of the present disclosure have been described in some detail for clarity of understanding, it will be apparent that certain changes and modifications can be made within the scope of the claims. Accordingly, the described embodiments are to be considered as illustrative and not restrictive, and the scope of the claims is not to be limited to details given herein, but can be modified within the scope and equivalents of the claims. In the claims, elements do not imply any particular order of operation, unless explicitly stated in the claims.

Many variations, modifications, additions, and improvements can be made. Plural instances can be provided for components, operations or structures described herein as a single instance. Boundaries between various components, operations and data stores are somewhat arbitrary, and particular operations are illustrated in the context of specific illustrative configurations. Other allocations of functionality are envisioned and can fall within the scope of the disclosure(s). In general, structures and functionality presented as separate components in exemplary configurations can be implemented as a combined structure or component. Similarly, structures and functionality presented as a single component can be implemented as separate components. These and other variations, modifications, additions, and improvements can fall within the scope of the appended claim(s).

The invention claimed is:

1. A computer-implemented self-enhancing clinical data prioritization and visualization system, the system comprising:
   a combiner module configured to retrieve information relating to a clinical context of a patient visit from a plurality of information sources;
   a prioritization module configured to prioritize contents of a display for a context-driven interface by:
     performing experience-driven statistical inference to generate priority estimates for different clinical information, wherein the priority estimates are used to determine placement of a plurality of visual blocks representing clinical data points within the context-driven interface; and performing machine interpretation of clinical guidelines to adjust the priority estimates for different clinical information by applying a plurality of document-driven rules to adjust the priority estimates generated by the experience-driven statistical inference; and a display module configured to generate the context-driven interface comprising a plurality of visual blocks arranged in a prioritized order based on their adjusted priority estimates for display, the context-driven interface configured to be customized by interacting with the context-driven interface by selecting and rearranging the visual blocks;

wherein the prioritization module in performing the experience-driven statistical inference is further configured to:

encode features of the retrieved information relating to a clinical context of a patient visit related to the clinical context into binary features to be input into a machine learning model;

instruct the machine learning model to generate priority estimates of observed data points using the encoded features to estimate priority of observed clinical data points; and iteratively adjust the machine learning model using a loss calculated by comparing the priority estimates against a priority index comprising historical physician behaviors and patient outcomes; and in response to determining that iterative adjustment of the machine learning model is complete, determine priority estimates for observed and unobserved data points in real time to be used to perform the machine interpretation of clinical guidelines.

2. The system of claim 1, wherein the combiner module is further configured to retrieve analytics information from analytics data sources to assemble an analytics model;

retrieve patient data from patient data sources; and combine the analytics model with the patient data for display in the context-driven interface.

3. The system of claim 1, wherein the prioritization module is further configured to:

receive user inputs from the context-driven interface;

monitor outcome metrics of the treatment generated by the system through usage of the context-driven interface; and adjust the priority estimate of the plurality of visual blocks based on the user inputs with the context-driven interface and the outcome metrics.

4. The system of claim 1, wherein the prioritization module in performing the experience-driven statistical inference is further configured to prioritize the retrieved information relating to a clinical context of a patient visit to a clinical context by fitting a non-parametric machine learning model to estimate the priority of observed data points in the retrieved information and unobserved data points in the retrieved information from clinical context information based on patterns from historical physician behaviors and contextually important patient outcomes.

5. The system of claim 1, wherein the prioritization module in performing the machine interpretation of clinical guidelines is further configured to adjust the priority estimates of each of the plurality of visual blocks in the context-driven interface from an experience-driven statistical inference based on dimensions of relevancy, abnormality, and quality, wherein relevancy indicates an extent to which a given data point is associated with a specified clinical context, wherein abnormality indicates whether the quantity associated with a clinical data point is unusual in magnitude for the specified clinical context, and wherein quality indicates an extent to which a clinical data point is expected to improve quality of care in the specified clinical context.

6. The system of claim 1, wherein the prioritization module in performing the machine interpretation of clinical guidelines is further configured to apply documented clinical guidelines retrieved by the combiner module to an observed clinical context to identify suggested care components along the dimensions of relevancy, abnormality, and quality.

7. The system of claim 6, wherein the prioritization module in performing the machine interpretation of clinical guidelines is further configured to extract, from the documented clinical guidelines, features based on the dimension of relevancy by:

tagging specific text in the documented clinical guidelines as recommendations and other text in the documented clinical guidelines as context and;

extracting features based on at least one or more of the presence of n-gram word combinations and by using natural language processing algorithms.

8. The system of claim 6, wherein the prioritization module in performing the machine interpretation of clinical guidelines is further configured to extract, from the documented clinical guidelines, features based on the dimension of abnormality by:

identifying specific diagnostics, medications, and prescriptions in the text of the documented clinical guidelines and parsing their associated normal values; and mapping the identified specific diagnostics, medications, and prescriptions from the text to an appropriate treatment to adjust the priority estimates generated by the experience-driven statistical inference.

9. The system of claim 6, wherein the prioritization module in performing the machine interpretation of clinical guidelines is further configured to extract, from the documented clinical guidelines, features based on the dimension of quality by:

codifying conditions when specific diagnostics, medications, and prescriptions in the text of the documented clinical guidelines are applicable by evaluating a quantitative value associated with each of the specific diagnostics, medications, and prescriptions in the context of a visiting patient; and increasing the priority estimate for the relevant codified condition when patient information corresponding to the visiting patient matches the codified condition.

10. The system of claim 1, wherein the combiner module is further configured to retrieve patient information by parsing audio data describing the patient, wherein the audio data is retrieved from one or more of audio recordings received from patients, physician audio recordings, and/or monitored audio dialog between doctors and patients.

11. The system of claim 3, wherein the user inputs comprise voice inputs to the context-driven interface and wherein the priority estimate of the plurality of visual blocks is adjusted based on whether the user input is a voice input.

12. A computer-implemented method for performing self-enhancing clinical data prioritization and visualization, the method comprising:

retrieving information relating to a clinical context of a patient visit from a plurality of information sources;

prioritizing, by a processor, contents of a display for a context-driven interface by:
  performing experience-driven statistical inference to generate priority estimates for different clinical information, wherein the priority estimates are used to determine placement of a plurality of visual blocks representing clinical data points within the context-driven interface; and
  performing machine interpretation of clinical guidelines to adjust the priority estimates for different clinical information by applying a plurality of document-driven rules to adjust the priority estimates generated by the experience-driven statistical inference; and
generating, by the processor, a display of the context-driven interface comprising a plurality of visual blocks arranged in a prioritized order based on their adjusted priority estimates, the context-driven interface configured to be customized by interacting with the context-driven interface by selecting and rearranging the visual blocks;
wherein performing the experience-driven statistical inference further comprises:
encoding, by the processor, features of the retrieved information relating to a clinical context of a patient visit related to the clinical context into binary features to be input into a machine learning model;
instructing, by the processor, the machine learning model to generate priority estimates of observed data points using the encoded features to estimate priority of observed clinical data points;
iteratively adjusting, by the processor, the machine learning model using a loss calculated by comparing the priority estimates against a priority index comprising historical physician behaviors and patient outcomes; and
in response to determining that iterative adjustment of the machine learning model is complete, determining, by the processor, priority estimates for observed and unobserved data points in real time to be used to perform the machine interpretation of clinical guidelines.

13. The computer-implemented method of claim 12, wherein retrieving the information further comprises:
  retrieving, by the processor, analytics information from analytics data sources to assemble an analytics model;
  retrieving, by the processor, patient data from patient data sources; and
  combining, by the processor, the analytics model with the patient data for display in the context-driven interface.

14. The computer-implemented method of claim 12, wherein the prioritizing further comprises:
  receiving, by the processor, user inputs from the context-driven interface;
  monitoring, by the processor, outcome metrics of the treatment generated by the system through usage of the context-driven interface; and
  adjusting, by the processor, the priority estimate of the plurality of visual blocks based on the user inputs with the context-driven interface and the outcome metrics.

15. The computer-implemented method of claim 12, wherein the performing the experience-driven statistical inference further comprises prioritizing, by the processor, the retrieved information relating to a clinical context of a patient visit to a clinical context by fitting a non-parametric machine learning model to estimate the priority of observed data points in the retrieved information and unobserved data points in the retrieved information from clinical context information based on patterns from historical physician behaviors and contextually important patient outcomes.

16. The computer-implemented method of claim 12, wherein performing the machine interpretation of clinical guidelines further comprises adjusting, by the processor, the priority estimates of each of the plurality of visual blocks in the context-driven interface from an experience-driven statistical inference based on dimensions of relevancy, abnormality, and quality, wherein relevancy indicates an extent to which a given data point is associated with a specified clinical context, wherein abnormality indicates whether the quantity associated with a clinical data point is unusual in magnitude for the specified clinical context, and wherein quality indicates an extent to which a clinical data point is expected to improve quality of care in the specified clinical context.

17. The computer-implemented method of claim 12, wherein performing the machine interpretation of clinical guidelines further comprises applying, by the processor, documented clinical guidelines retrieved by a combiner module to an observed clinical context to identify suggested care components along the dimensions of relevancy, abnormality, and quality.

18. The computer-implemented method of claim 17, wherein performing the machine interpretation of clinical guidelines further comprises extracting, by the processor and from the documented clinical guidelines, features based on the dimension of relevancy by:
  tagging, by the processor, specific text in the documented clinical guidelines as recommendations and other text in the documented clinical guidelines as context and;
  extracting, by the processor, features based on at least one or more of the presence of n-gram word combinations and by using natural language processing algorithms.

19. The computer-implemented method of claim 17, wherein performing the machine interpretation of clinical guidelines further comprises extracting, by the processor and from the documented clinical guidelines, features based on the dimension of abnormality by:
  identifying, by the processor, specific diagnostics, medications, and prescriptions in the text of the documented clinical guidelines and parsing their associated normal values; and
  mapping, by the processor, the identified specific diagnostics, medications, and prescriptions from the text to an appropriate treatment to adjust the priority estimates generated by the experience-driven statistical inference.

20. The computer-implemented method of claim 17, wherein performing the machine interpretation of clinical guidelines further comprises extracting, by the processor and from the documented clinical guidelines, features based on the dimension of quality by:
  codifying, by the processor, conditions when specific diagnostics, medications, and prescriptions in the text of the documented clinical guidelines are applicable by evaluating a quantitative value associated with each of the specific diagnostics, medications, and prescriptions in the context of a visiting patient; and
  increasing, by the processor, the priority estimate for the relevant codified condition when patient information corresponding to the visiting patient matches the codified condition.

21. The computer-implemented method of claim 12, wherein retrieving information relating to a clinical context of a patient visit further comprises retrieving patient information by parsing audio data describing the patient, wherein the audio data is retrieved from one or more of audio recordings received from patients, physician audio recordings, and/or monitored audio dialog between doctors and patients.

22. The computer-implemented method of claim 14, wherein the user inputs comprise voice inputs to the context-driven interface and wherein the priority estimate of the plurality of visual blocks is adjusted based on whether the user input is a voice input.

* * * * *